United States Patent [19]

Tartaglia

[11] 4,318,313
[45] Mar. 9, 1982

[54] TWEEZER FORCEPS

[76] Inventor: John A. Tartaglia, 108 Stoddard Rd., Waterbury, Conn. 06701

[21] Appl. No.: 128,567

[22] Filed: Mar. 10, 1980

[51] Int. Cl.³ .................. B25B 9/02; A61B 17/30
[52] U.S. Cl. ............................ 81/43; 128/354
[58] Field of Search ............... 128/354, 321, 346; 81/43, 428 R; 433/157, 162; D28/55

[56] References Cited

U.S. PATENT DOCUMENTS

| 561,176 | 6/1896 | Parker | 81/43 X |
| 1,198,958 | 9/1916 | Risley | 128/354 |
| 1,380,232 | 5/1921 | Metcalf | 128/354 |
| 1,741,457 | 12/1929 | Glass | 128/325 |
| 3,648,702 | 3/1972 | Bean | 128/321 |
| 4,212,305 | 7/1980 | Lahay | 128/354 |

Primary Examiner—Michael H. Thaler
Attorney, Agent, or Firm—St. Onge, Steward, Johnston, Reens & Noe

[57] ABSTRACT

Tweezer forceps in which the gripping arms and end section at which they are joined are formed of a single sheet of resilient sheet material, the arms and end section forming an integral spring-element disposed within the plane of the sheet material, such that the arms flex edgewise into and out of gripping engagement at their tips. Finger pieces are provided on the arms for engagement by the user's fingers when squeezing them together. Provision may also be made for aligning the arms against lateral displacement, and a jaw-locking device may be provided.

4 Claims, 9 Drawing Figures

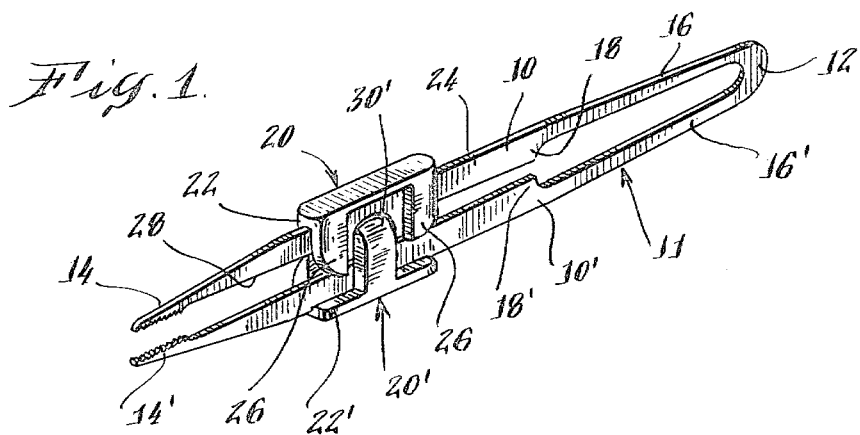
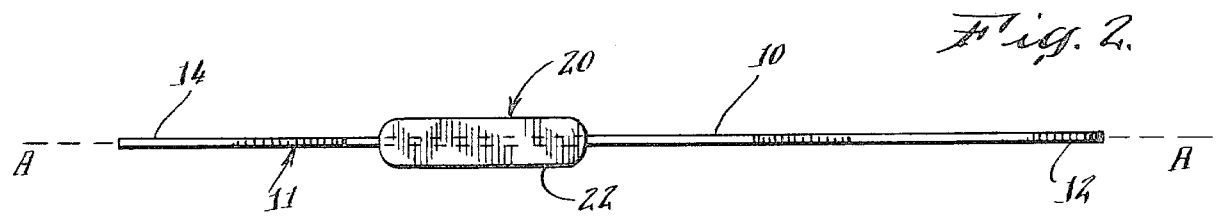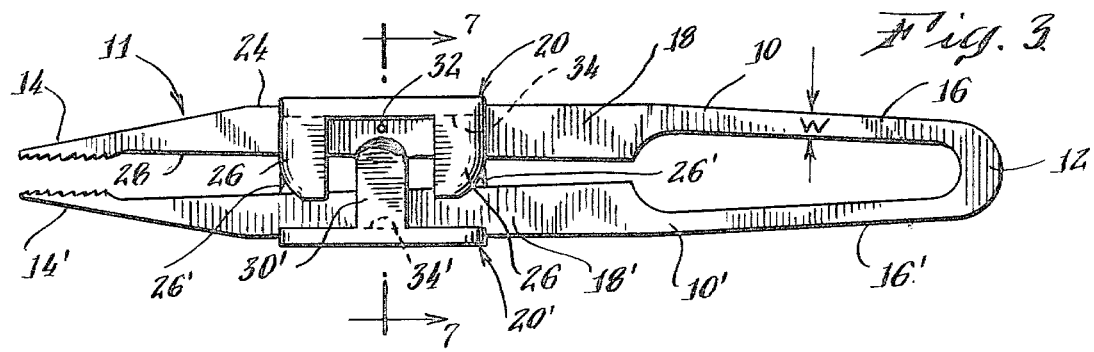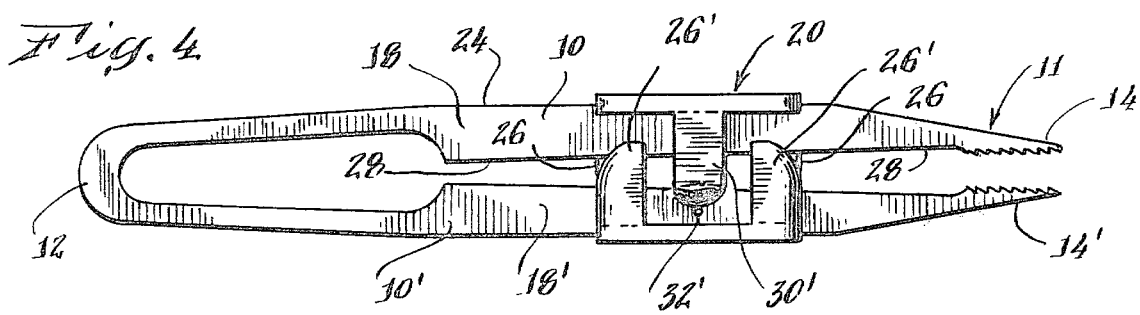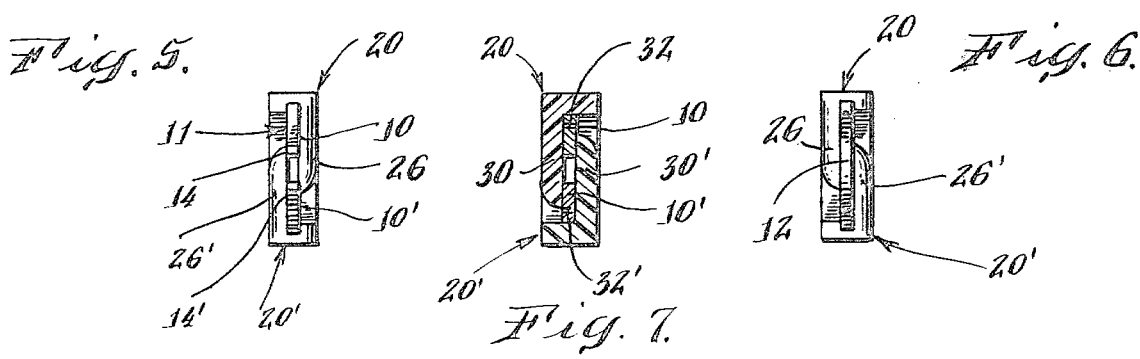

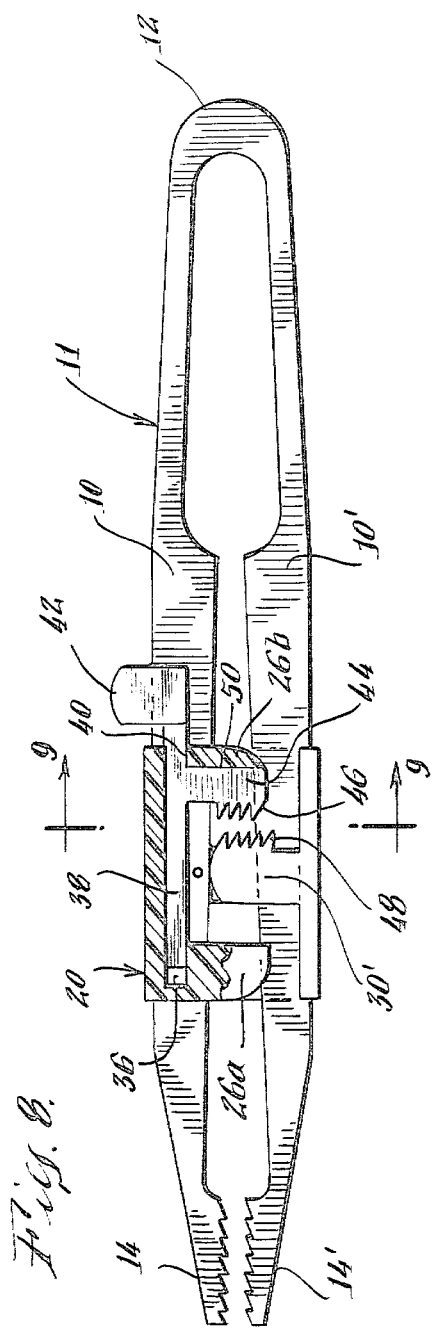
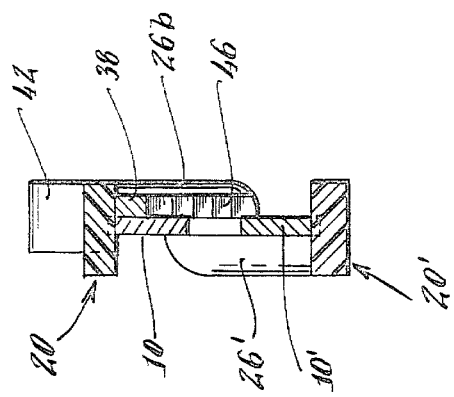

TWEEZER FORCEPS

FIELD OF THE INVENTION

The invention relates to forceps or pincers, and it relates more particularly to tweezer-type forceps, in which a pair of arms are integrally joined at one end and spaced throughout their length so that when they are pressed together their tips tightly engage in order to sieze and hold an object between them.

DESCRIPTION OF THE PRIOR ART

Forceps of this type are well known and are usually made of metal when they are to be resterilized after use, or of plastic when they are to be discarded. Examples of disposable medical forceps made of plastic are shown in U.S. patents to Whitton, Jr. et al U.S. Pat. No. 3,140,715, Eizenberg U.S. Pat. No. 3,367,336, Bean U.S. Pat. No. 3,648,702, Shannon U.S. Pat. No. 3,653,389, Huston et al U.S. Pat. No. 3,977,410 and Wannog U.S. Pat. No. 4,044,771. The arms of the forceps in each of these patents are generally T-shaped in cross-section and are hinged together at one end by flat sections which are formed by extensions of the flat cross-portion of each arm. In a similar type of gripping device illustrated in U.S. Pat. No. to Johnson 4,009,899, the arms are formed with a flat strap portion having outwardly extending ribs along its edges. Attention is also directed to the plastic forceps disclosed in U.S. Pat. No. 3,906,957 to Weston, in which the arms are flat and are provided with a strengthening ridge along their inner surfaces.

In each of the devices shown in the above-noted patents, as in the conventional tweezer-type of forcep illustrated, for example, in the U.S. Pat. No. to Johnson 2,082,062, the arms are flat, the greater dimension of each extending generally parallel to that of the other arm. Where the arms are strengthened longitudinally by ribs, they are joined or hinged at one end by a relatively thin section which permits the arms to flex in this hinge-section instead of over their full length. In order to make metal forceps of prior designs, it has been necessary to employ relatively costly manufacturing techniques, which have placed them at a distinct competitive disadvantage with respect to other types of forceps, especially of the so-called throw-away kind.

An object of the present invention is to provide tweezer-type forceps which can be produced in large quantities by a simple stamping operation, which eliminates the costly and time-consuming manufacturing operations required heretofore. Another object of the invention is to provide a reliable way of aligning the tips of the arms of the forceps when they are pressed together, in order to positively grip an object. Still another object is to provide a lock for holding the tips or gripping jaws of the forceps together, so that they do not release the object when finger pressure is relaxed. These and other objects of the invention will become more apparent from the detailed description hereinafter of certain preferred embodiments thereof.

SUMMARY OF THE INVENTION

The invention resides in making tweezer forceps from a single sheet of resilient, relatively thin sheet material, both arms being resiliently movable edgewise toward each other when gripping an object between them. In order to facilitate manipulation, finger means are provided intermediate the ends of each arm adjacent the outer edge thereof, so that the fingers of the user do not press directly against the narrow edges of the arms when they are squeezed together to grip an object.

In a particularly desirable form of the invention, the finger means comprise separately mounted pieces for each arm, each such finger piece providing a pad disposed across the edge of the arm, against which the user can press. In addition, the finger pieces are desirably provided with guide projections that fit close to the sides of both arms of the forceps for maintaining them in alignment with each other when they are pressed together edgewise.

DETAILED DESCRIPTION OF THE PREFERRED EMBODIMENTS OF THE INVENTION

With the foregoing general background and summary of the invention, as well as objects and advantages thereof in mind, the invention will be more fully understood from the description hereinafter of the best modes known at this time for carrying out the invention, reference being had to the accompanying drawing, wherein:

FIG. 1 is a perspective view of tweezer forceps embodying the invention;

FIG. 2 is a top plan view thereof;

FIG. 3 is a side elevational view thereof;

FIG. 4 is a side elevational view from the side opposite that shown in FIG. 3;

FIG. 5 is an end elevational view looking toward the tips of the forceps, in other words as viewed from right to left in FIG. 4;

FIG. 6 is a rear end elevational view;

FIG. 7 is a cross-sectional view taken on the line 7—7 and looking in the direction of the arrows;

FIG. 8 is a side elevational view, partially in section, of forceps similar to those shown in FIGS. 1-7, but showing the addition of a jaw-locking device; and FIG. 9 is a cross-sectional view taken on the line 9—9 in FIG. 8 and looking in the direction of the arrows.

In the drawings forceps in accordance with the invention are formed primarily from a sheet of relatively thin sheet-material, preferably sheet-metal, each unit including a pair of elongated arms 10, 10' integral with an end section 12. Arms 10, 10' and their integral end section 12 form an elongated U-shaped tweezer-like spring element 11, which can be produced very easily using large-scale production stamping machines. The free ends or tips 14, 14' of arms 10, 10', which are biased to an open or spaced position, may be provided with gripping teeth for securely grasping an object when the arms 10, 10' are flexed toward each other to engage tips 14, 14'. Spring-element 11 lies entirely within a common plane A—A (FIG. 2), within which its arms 10, 10' are movable edgewise into and out of gripping engagement with each other at their tips 14, 14'. It will be noted that each arm 10 is substantially wider at its narrowest point than the thickness or gauge of the sheet-material from which it is made.

The resistance to flexing is of course determined not only by the gauge and physical characteristics of the material used, but also by the width w of arms 10, 10' in their sections 16, 16' adjacent the end-section 12. The mid-portions 18, 18' of the arms are substantially wider than the sections 16, 16' where most of the bending occurs, the width w of sections 16, 16' being, nevertheless, several times greater than the thickness of the material. The width of the mid-portions 18, 18' of arms 10, 10' should be greater than the width w of spring portions 16, 16', in order to make the spring-element 11 substantially rigid in the middle, thereby increasing the pressure applied at tips 14, 14' and optimizing their gripping action.

In order to facilitate manipulation of the forceps, finger pieces 20, 20' are mounted on the mid-portions 18, 18' of arms 10, 10' at a suitable distance rearward of their tips 14, 14'. Finger pieces 20, 20' are desirably separate from the spring-element 11 and are provided with means for preventing them from being accidentally detached therefrom. In this instance finger pieces 20, 20' are identical, each having an elongated finger pad 22, disposed across the outer edge 24 of the arm on which it is mounted, as for example arm 10, with a pair of projections 26, 26 extending inward from the pad portion 22 on one side of such one arm 10. Projections 26, 26 are spaced from each other longitudinally of the arm 10, with the ends of both of projections 26, 26 extending well beyond the inner edge 28 of the one arm 10 into overlapping relation with the other arm 10'.

A single projection 30 (FIGS. 4 and 7) is provided on finger piece 20 intermediate projections 26, 26 and parallel thereto, but on the opposite side of the one arm 10. The end of projection 30 likewise extends beyond the inner edge 28 of arm 10 into overlapping relation with the corresponding side of arm 10'.

Finger piece 20' is similarly provided with a pair of corresponding projections 26', 26', which straddle the single projection 30 of finger piece 20, on one side of arm 10', and with a corresponding single projection 30' on the other side of arm 10', which is disposed between the two projections 26, 26 of finger piece 20. In addition, when the arms 20, 20' are apart in their untensioned or rest position, as shown in the drawings (i.e., tips 20, 20' are open), the ends of projections 26 or 26' and 30 or 30' on the respective finger pieces are spaced from the inner side of the pad portion 22 or 22' of the other finger piece, so that they do not engage when the arms 10, 10' are flexed inwardly to tightly engage tips 14, 14'. Manual pressure required to pinch the arms together is applied by squeezing the finger-pieces 20, 20' together between the thumb and one or more fingers of the person using them. Arms 10, 10' fit snuggly at their outer edges between the respective projections 26 or 26' on one side and the single projection 30 or 30' on the other, the outer ends of such projections being disposed close to, if not actually engaging, the sides of the opposite arm, thereby confining it within the plane A—A and maintaining both arms and their tips 14, 14' in exact alignment with each other.

In order to prevent the finger pieces 20, 20' from accidentally becoming detached from their respective arms 10, 10', a small hole 32 (FIGS. 3, 4 and 7) is provided in each arm adjacent the projections 30, 30', against which is pressed the end of a small retaining teat or protrusion on the inner surface of each projection 30, 30', each protrusion being located such that it is aligned with the respective hole 32, 32' on the corresponding arm 20 or 20' when its pad 22, 22' is pressed tightly against the outer edge of the arm on which it is mounted. Thus, since the spacing between the single projection 30, 30' and the pair of projections 26, 26 or 26', 26' laterally of arms 10, 10' on each finger piece 20, 20' is the same as the thickness of the arms, the retaining teats on projections 30 and 30' are held firmly against the portion of the arm 10 or 10' surrounding the corresponding holes 32 and 32'. Accordingly, each finger piece 10, 10' firmly grips its respective arm 10, 10', preventing it from being accidentally dislodged. Finger pieces 20, 20' may be readily molded from a suitable plastic material, which should be rigid enough to ensure proper guidance of the arms 10, 10' between guide projections 26, 26', 30, 30' while being tough enough to allow the retaining teats on projections 30, 30' to be distorted when the finger pieces are being assembled yet function to retain the finger pieces on the arms of the spring-element 11.

In addition, finger-pieces 20, 20' are positively prevented from moving lengthwise on arms 10, 10' by elongated notches 34, 34' in the outer edges 24 of each arm, notches 34, 34' being the same length as finger pieces 20, 20' which fit snugly within them when their respective retaining teats are engaged in holes 32, 32'.

FIGS. 8 and 9 show tweezer-forceps similar to those of FIGS. 1–7, but in which a locking device is provided for holding the arms 10, 10' and tips 14, 14' in their gripping position, so that manual pressure on the finger pieces 20, 20' can be released without allowing the jaws to open. In this arrangement one of the finger pieces (for example finger piece 20) is provided with a short, rectangular guideway 36 on the inner surface of the projection 26a nearest the tips 14, 14' of the spring-element 11. Guideway 36 is open at the rear edge of projection 26a to receive the rectangular end of an elongated locking member 38, which is slidable longitudinally into and out of its locking position. The rear end of locking member 38 is slidably supported in a guideway 40 on the inner surface of the rear projection 26b of finger piece 20. Guideway 40 extends completely through the projection 26b, so that locking member 38 can extend rearward of finger piece 20, where it is provided with an upstanding thumb piece 42 by which to manually slide member 38 into and out of its locking position.

Depending from the elongated portion of locking member 38 is a foot 44 having locking teeth 46 on its front edge which, on movement of member 18 forward (to the left as viewed in FIG. 8), lock with corresponding teeth 48 on the rear edge of the single projection 30' on the other fingerpiece 20'. Both sets of teeth 46 and 48 should be shaped so that one side of each tooth is substantially horizontal in order to ensure that they do not accidentally disengage under the spring-pressure of arms 10, 10' when manual pressure is relaxed. In order to provide operating room for the locking foot 44, projection 26b is partially cut away on its inner side, leaving its outer surface and a rear portion 50, against which foot 44 abuts when locking member 38 is in its unlocked position as illustrated in FIG. 8.

The locking forceps of FIGS. 8 and 9 are used in the same manner as those shown in FIGS. 1–7, except that when the arms 10, 10' are squeezed together to grasp an object, they can be locked in this position by shifting the locking member 38 on finger piece 30 forward to its locking position. In this position teeth 46 lock with teeth 48 on the center projection 30' of the other finger piece 20', thereby preventing separation of arms 10 and 10' so that the user can let-go of the forceps without releasing the grip of the forceps. They can then be passed from one hand to another, from one person to another, or simply set aside, without releasing the object gripped between the tips 14, 14'.

It should be noted that the projection 30' is shorter than its counterpart in FIGS. 1–7, in order to provide space between the upper end of projection 30' and the lower edge of locking member 38, thereby allowing clearance when finger pieces 20, 20' are squeezed together to close the jaws of the forceps.

I claim:

1. In tweezer forceps comprising a spring element having a pair of elongated arms projecting longitudinally from and integral with an end section by which they are joined, said arms being normally spaced throughout their length from said end section to their free ends and having tips adjacent said free ends which are engageable upon flexing said arms toward each other for gripping an object, the improvement wherein said spring-element is formed from a single sheet of resilient relatively thin sheet material of uniform thickness defining a common plane, the minimum width of said arms in the direction of flex being substantially greater than the thickness of the material, said arms being resiliently flexible edgewise toward each other within said plane, finger pieces attached intermediate the ends of each of said arms adjacent the outer edge thereof, against which the fingers of the user are pressed in order to flex said arms inwardly to grip an object with the tips of said arms, said finger pieces being of identical configuration so as to be interchangeable on said arms and each having a finger pad with an engagement surface against which the user can press a finger, said finger pad being disposed against said outer edge of said arm and said engagement surface extending transversely of said plane, each said finger piece including means for aligning the tips of said arms and for maintaining such alignment throughout their movement, wherein said alignment means comprises a first projection on each of said finger pieces extending from said finger pad toward the other finger piece closely adjacent and parallel to one side of the one said arm on which it is mounted, and a pair of projections spaced longitudinally of said one arm and extending from said finger pad closely adjacent the opposite side of such one arm parallel to said first projection, said first projection being positioned intermediate said pair of projections longitudinally of said arm, said projections on each of said finger pieces extending beyond the inner edge of said one arm for guiding engagement with the corresponding side of the other arm, said finger pieces being mounted on their respective arms such that said first projection on each is received between said pair of projections on the other, whereby to maintain alignment of said arms within said common plane in all operating 2. Tweezer forceps as defined in claim 1, which further includes jaw-locking means comprising an elongated locking member mounted on one of said finger pieces for sliding movement longitudinally of said arms into and out of locking position, said locking member having a foot portion extending laterally thereof into working relationship with one side of said first projection on the other of said finger pieces, one of said foot portion and said first projection having a series of locking teeth and the other at least one corresponding locking tooth in confronting relation thereto for intermeshing engagement therewith when said locking member is slid into its said locking position to maintain said jaws locked in fixed position relative to each other in their range of operative movement.

3. Tweezer forceps as defined in claim 1, which further includes means for resiliently attaching said finger pieces to said arms comprising a teat extending laterally from the inner surface of said first projection of each of said finger pieces and a hole through each of said arms for receiving said teat, said hole and teat being disposed such that when said finger pad is positioned against said outer edge of said arm said teat is disposable within said hole.

4. Tweezer forceps as defined in claim 1, which further includes an elongated notch on said outer edge of said arm in which said finger pad fits for positively preventing longitudinaly movement of said finger piece with respect to said arm.

* * * * *